United States Patent [19]

Arbige et al.

[11] Patent Number: 4,726,954

[45] Date of Patent: * Feb. 23, 1988

[54] LIPOLYTIC ENZYME DERIVED FROM A ASPERGILLUS MICROORGANISM HAVING AN ACCELERATING EFFECT ON CHEESE FLAVOR DEVELOPMENT

[75] Inventors: Michael V. Arbige, Bensalem; Clifford E. Neubeck, Hatboro, both of Pa.

[73] Assignee: Genencor, Inc., South San Francisco, Calif.

[ * ] Notice: The portion of the term of this patent subsequent to Jan. 13, 2004 has been disclaimed.

[21] Appl. No.: 932,815

[22] Filed: Nov. 18, 1986

Related U.S. Application Data

[63] Continuation of Ser. No. 623,931, Jun. 25, 1984, Pat. No. 4,636,468.

[51] Int. Cl.$^4$ .......................... A23C 9/12; C12N 9/20; C12N 1/14; C12R 1/66
[52] U.S. Cl. ..................................... 426/35; 435/198; 435/254; 435/913
[58] Field of Search ......... 435/198, 254, 913; 426/35

[56] References Cited

U.S. PATENT DOCUMENTS

| | | | |
|---|---|---|---|
| 3,634,195 | 1/1972 | Melachouris et al. | 435/198 |
| 3,975,544 | 8/1976 | Kosikowski | 426/35 |
| 4,065,580 | 12/1977 | Feldman et al. | 426/35 X |

OTHER PUBLICATIONS

Borgstrom et al., eds. Lipases, 1984, pp. 443, 455–457, 466–469.

*Primary Examiner*—Lionel M. Shapiro
*Attorney, Agent, or Firm*—James G. Passe

[57] ABSTRACT

The present invention relates to a novel lipolytic enzyme derived from a novel Aspergillus microorganism. Cheese aged in the presence of a low concentration of this lipolytic enzymes ripens faster than with conventional lipolytic enzymes and without any associated rancidity.

8 Claims, 14 Drawing Figures

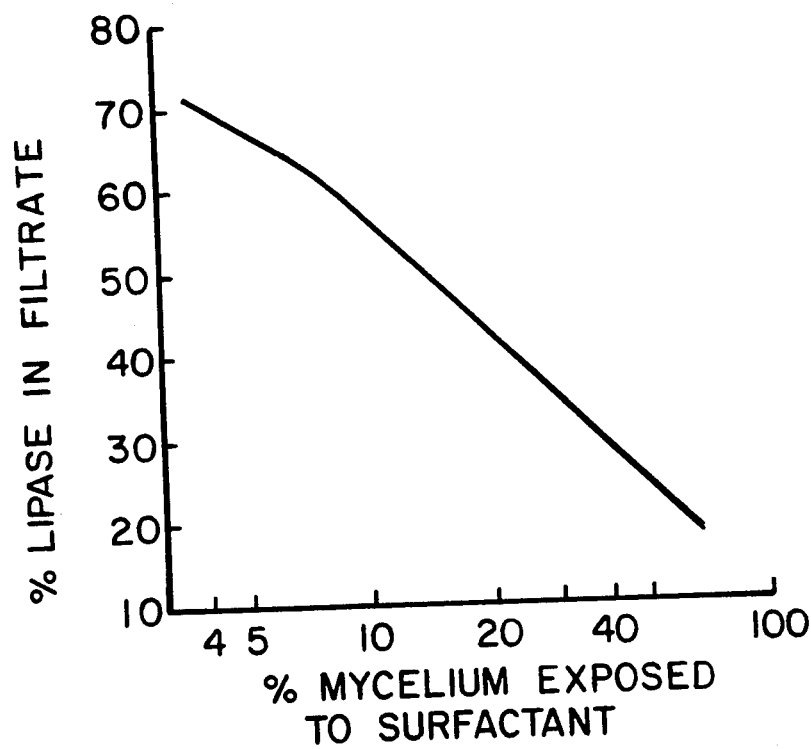
Fig. 1 — EFFECT OF MYCELIUM CONCENTRATION ON RELEASE OF LIPASE FROM MYCELIUM
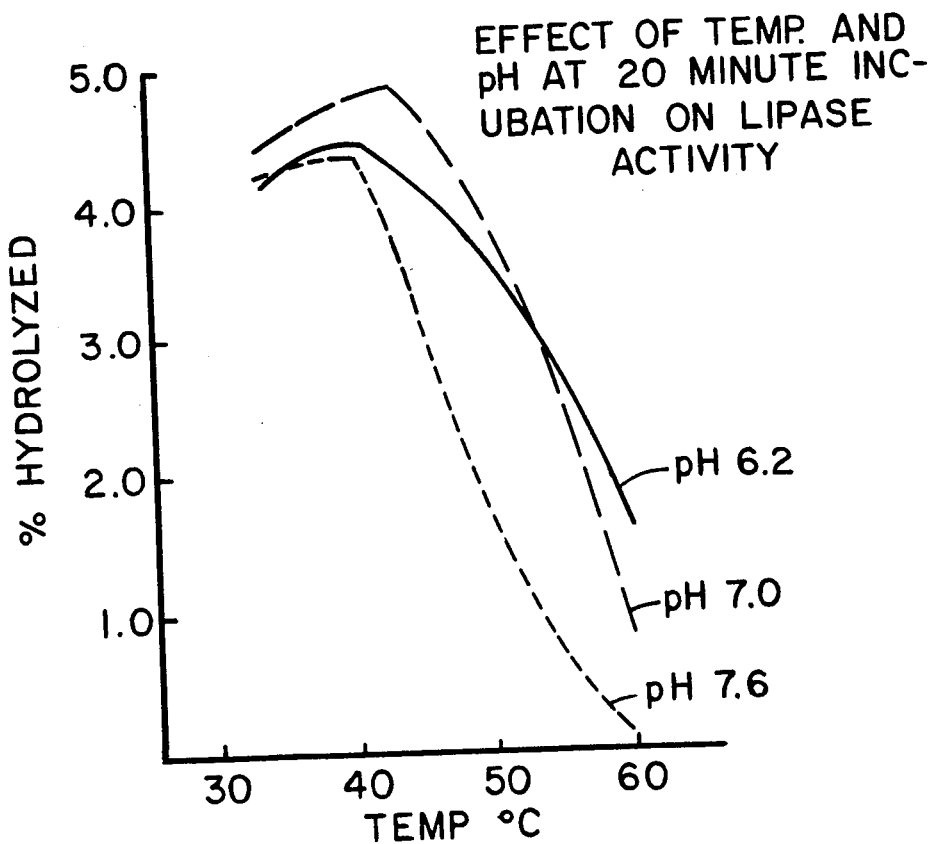
Fig. 4 — EFFECT OF TEMP. AND pH AT 20 MINUTE INCUBATION ON LIPASE ACTIVITY

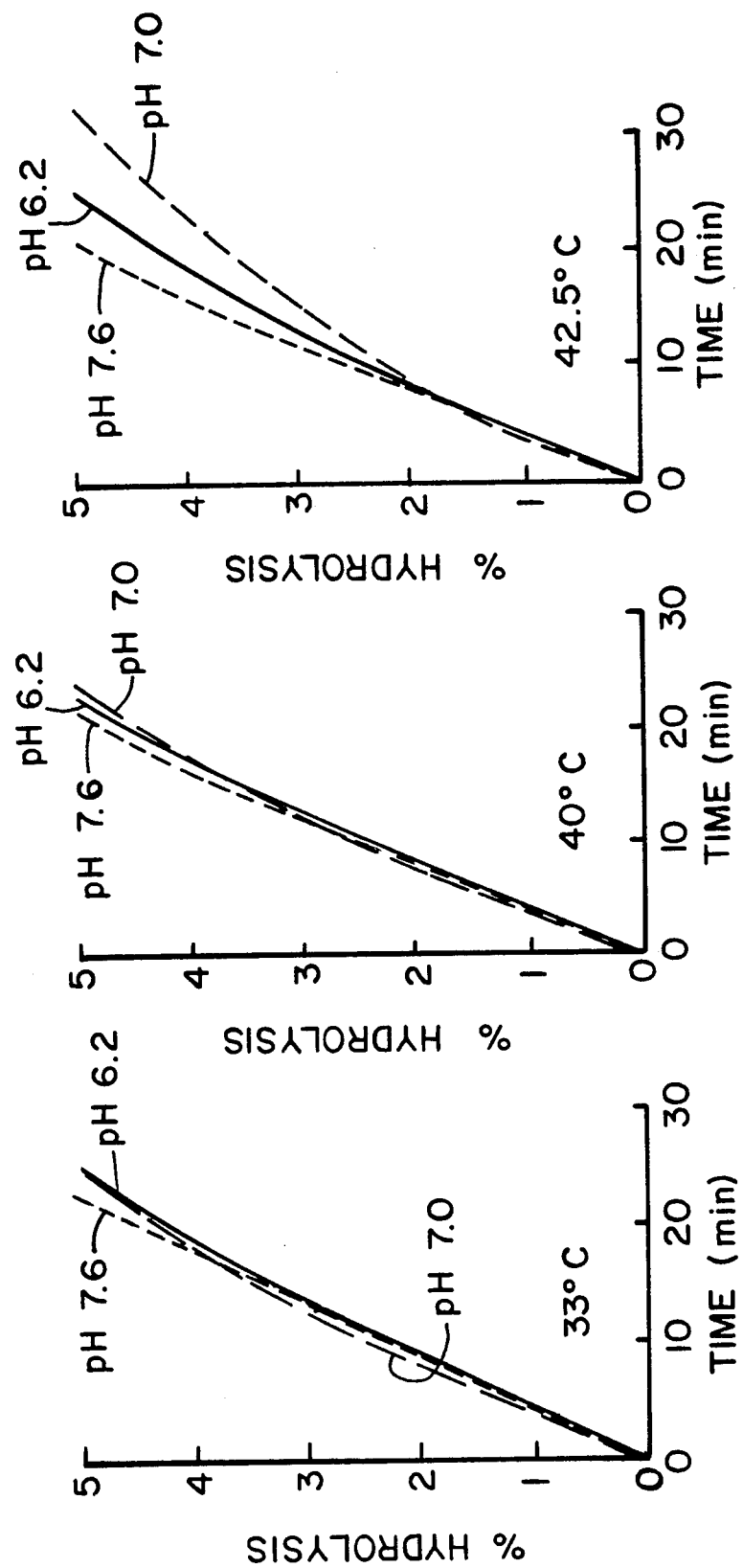

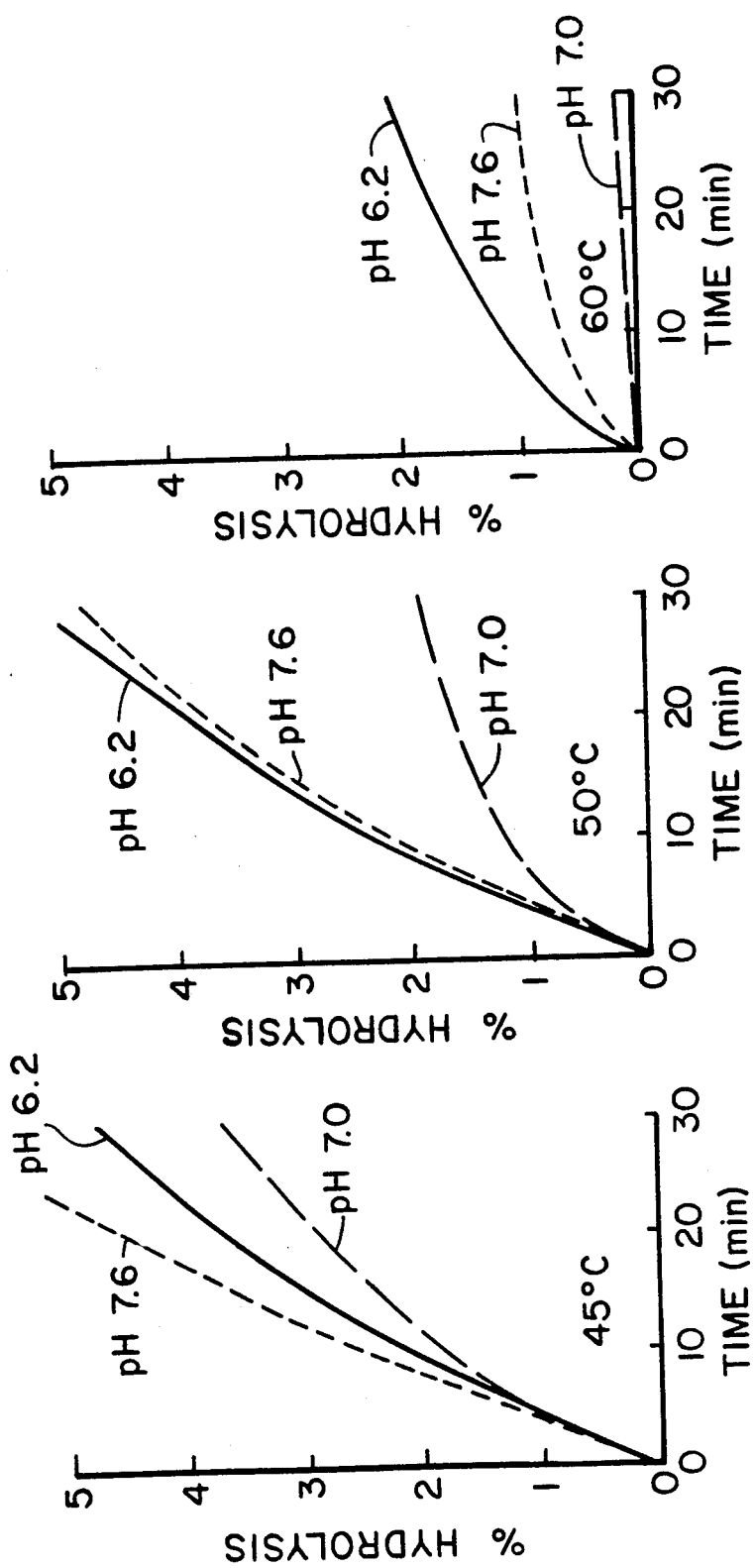

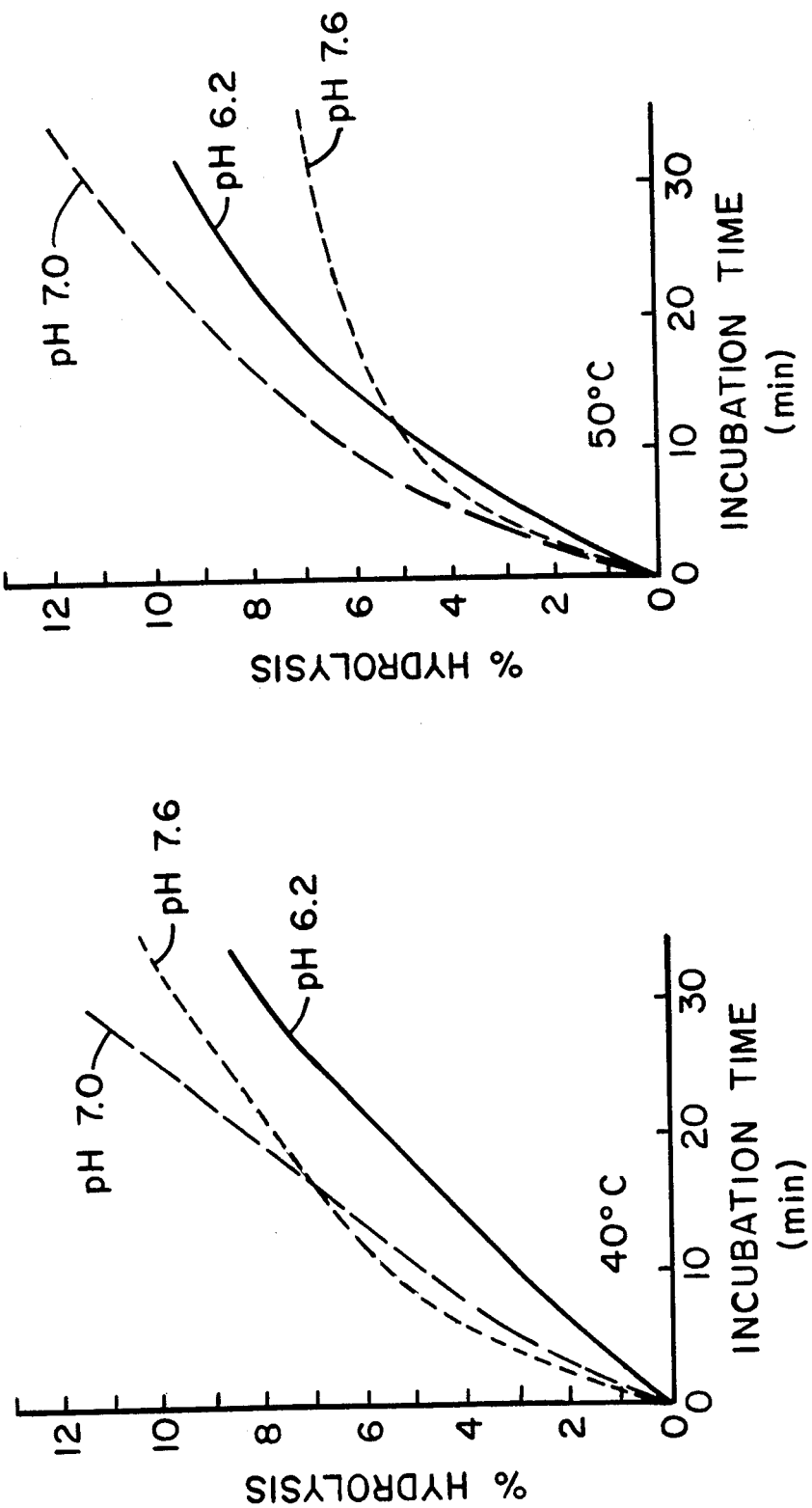

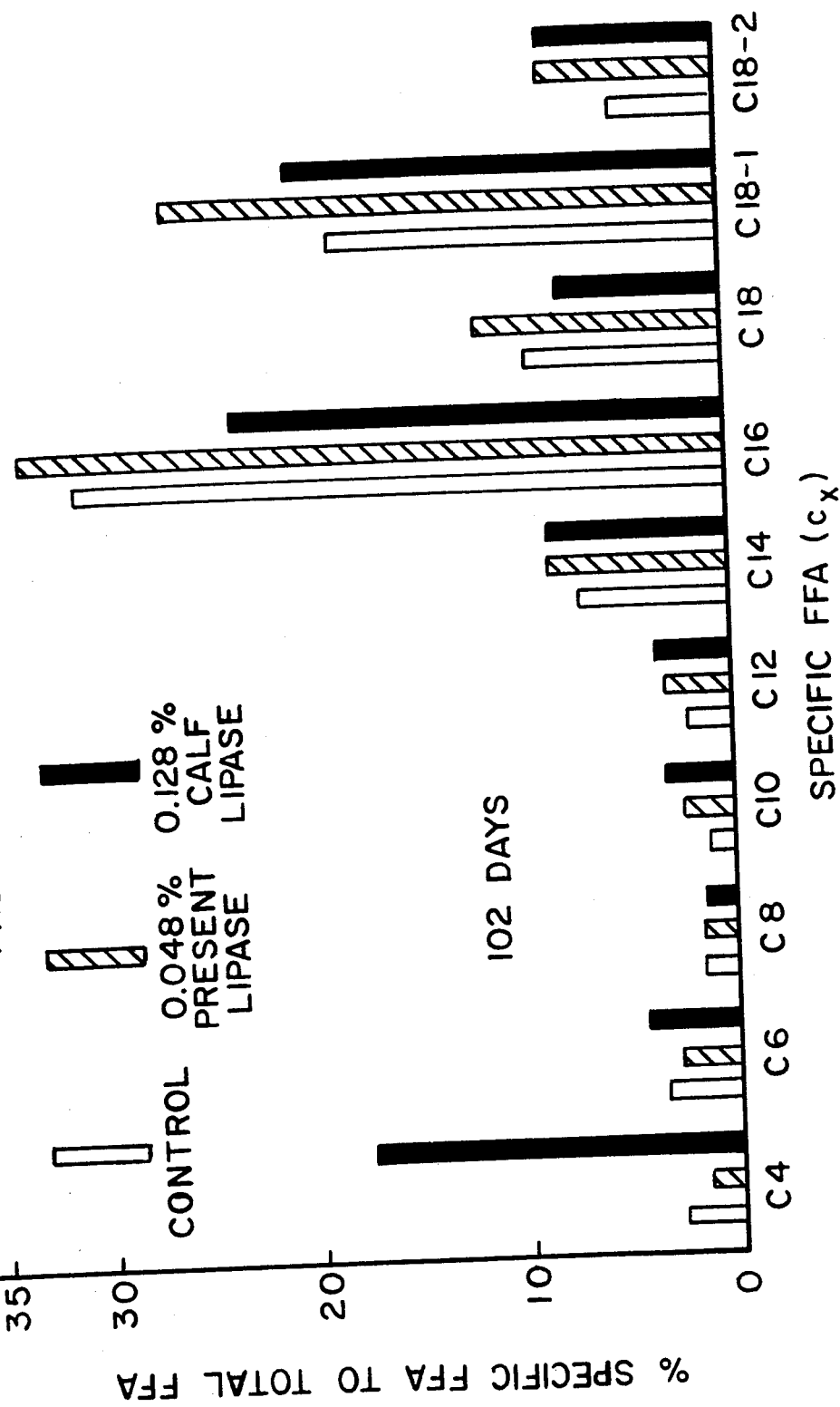

LIPOLYTIC ENZYME DERIVED FROM A ASPERGILLUS MICROORGANISM HAVING AN ACCELERATING EFFECT ON CHEESE FLAVOR DEVELOPMENT

This application is a continuation of application Ser. No. 623,931, filed June 25, 1984.

TECHNICAL FIELD

The present invention relates to a novel lipolytic enzyme derived from a novel Aspergillus microorganism. Cheese aged in the presence of a low concentration of this lipolytic enzyme ripens faster than with conventional lipolytic enzymes and without any lipolytic enzyme-associated rancidity.

BACKGROUND ART

Accelerating of cheese aging to improve cost efficiency through a reduction of storage space is becoming more important to the cheese industry. Currently, lipases from two different sources, animal pregastric glands, and animal pancreases, are being added to cheese curd as accelerators. A third source, microbial lipases, has not yet been used in commercial production of strongly flavored cheeses, but not mild cheeses.

Lipases derived from the pregastric gland of kid, calf and lamb are currently being added to accelerate ripening in cheese of Italian type (Provolone, Romano, Parmesan) where the characteristic rancid flavor of low molecular weight free fatty acids (e.g. butyric acid) is desirable. However, when these pregastric lipases are used to accelerate mild flavored cheese, e.g. Cheddar, too much of the low molecular weight fatty acids are produced and a rancid flavor develops. When the animal pancreas lipases are used in a high concentration, excessive amounts of lauric acid is produced in the cheese, making a soapy taste. Moreover, unless highly purified, these lipases can contain an abundance of protease which although in small amounts aids cheese softening, in larger amounts it produces bitter off-flavors.

In the search for lipases showing desirable ripening characteristics, numerous organisms such as *Pseudomonas fragii, P. fluorescens, Staphylococcus aureus, Clostridium lipolytica, Geotrichium candidum, Penicillium roqueforti, Aspergillus niger, A. flavus, A. oryzae, Candida cylindracea* and *Rhizopus oligosporous*, have been used in laboratory studies. Many of these microbial lipases are not yet available commercially. In a study of various lipases for cheese ripening, Harper, W. J., [J. Dairy Science 40 556 (1957)], the following data has been developed with respect to selective liberation of free fatty acids from 20% butterfat cream.

TABLE 1

| Lipase Source | Release of Free Fatty Acid from 20% Butterfat Cream | | | | |
|---|---|---|---|---|---|
| | Mol. Butyric | % Produced in 3 hrs. Caproic | Caprylic | @ 35 C Capric | Lauric |
| Imported kid rennet (paste) Pregastric esterases | 32.8 | 11.3 | 7.1 | 11.8 | 33.6 |
| kid | 44.4 | 15.2 | 7.6 | 12.3 | 21.5 |
| lamb | 48.1 | 8.6 | 14.2 | 9.3 | 19.3 |
| calf | 36.7 | 8.9 | 14.8 | 10.7 | 39.0 |
| Domestic calf rennet | 10.7 | 3.1 | trace | trace | 86.5 |
| Milk lipase | 13.5 | 8.2 | 10.2 | 8.7 | 60.0 |
| Pancreatic lipase | 8.4 | 2.1 | trace | trace | 89.1 |

TABLE 1-continued

| Lipase Source | Release of Free Fatty Acid from 20% Butterfat Cream | | | | |
|---|---|---|---|---|---|
| | Mol. Butyric | % Produced in 3 hrs. Caproic | Caprylic | @ 35 C Capric | Lauric |
| *A. niger* lipase | 43.1 | 18.9 | 20.2 | 17.5 | trace |

Little information is available on the relationship between specific free fatty acids and flavor intensity in cheese although the presence of butyric acid usually is associated with strong rancidity development in strong cheese and the presence of large amounts of lauric may lead to a soapy flavor. Longer chain fatty acids have been linked to fruity flavors. It is generally noted that all of the even numbered free fatty acids are present but the concentration of the specific fatty acids varies in different types of cheese.

DISCLOSURE OF THE INVENTION

The present invention relates to isolated cultures of a selected mutant strain of Aspergillus fungus. When cultured in a suitable nutrient medium, under proper aeration and agitation, it produces a novel lipolytic enzyme. For the purposes of this disclosure, this type of enzyme shall be referred to as a lipase although esterases are included in this term. lipase.

Fungus

The instant fungus has been identified as a novel strain of Aspergillus. The present fungus has been deposited in the American Type Culture Collection.

Enzyme

The present Aspergillus organism makes a novel and especially useful lipase when cultured in an oil-based medium the same manner as known Aspergillus organisms. However, the lipase from the present Aspergillus. organism hydrolyzes longer chain $C_6$ and $C_8$ triglycerides such as tricaproin and tricaprylin more efficiently than short chain $C_4$ triglycerides such as tributyrin.

Lipase having this characteristic appears to be useful as a ripening accelerator in mild flavored cheese production, such as Cheddar cheeses. The less efficient hydrolysis of the shorter $C_4$ triglycerides suppresses the development of rancid flavors which are unwanted in mild cheeses.

When isolated from the present Aspergillus organism under proper dilution, agitation, pH, and salt concentration conditions, the present lipase is associated with low levels of protease which soften the cheese without producing bitter flavors.

BRIEF DESCRIPTION OF THE DRAWINGS

FIG. 1 is a graph showing the effect of mycelium concentration on lipase release.

FIG. 4 is a graph showing the effect of temperature on lipase activity at various pHs.

FIG. 5a–f are graphs showing the effect of time on lipase activity at various temperatures and pHs.

FIG. 6 is a graph showing the effect of time on tricaprylin hydrolysis by the present lipase at 40° C.

FIG. 7 is a graph showing the effect of time on tricaprylin hydrolysis by the present lipase at 50° C.

FIG. 9 is a graph showing the percent hydrolysis of a specific free fatty acid to total free fatty acid in enzyme-added cheeses.

MODES FOR CARRYING OUT THE INVENTION

Culturing the Organism

Figure 2:
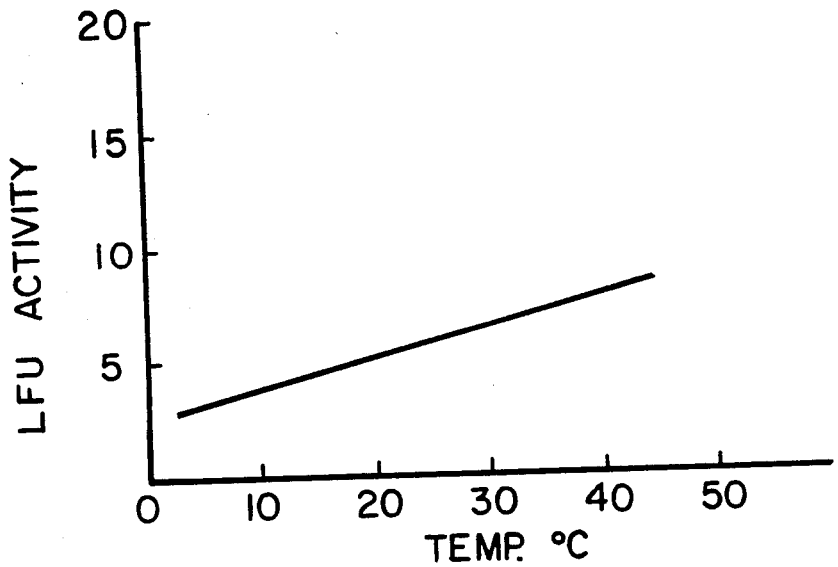
FIG. 2 is a graph showing the effect of temperature on lipase activity at pH 6.2.

The Aspergillus organism is stored in sterile soil under refrigeration. Portions of the soil stock are transferred to potato dextrose agar (PDA) and grown 4-5 days at 20°-35° C., 30° C. preferably, to use as primary inoculum for shake flask and fermenter growth.

Lipase can be made in a shaker flask by inoculating directly from the PDA slant into 100 ml. of sterile medium at pH 5.1 (5.0-5.2) containing 6% soy bean meal, 5% monobasic ammonium phosphate, 0.5% Magnesium sulfate (crystal), 2% soy oil, 1L Erlenmeyer flasks. After 3-5 days at 30° C. and an agitation of 265 RPM, the culture is filtered. Preferred ranges for culture ingredients are: 1-10% oil; >0.1-1% sulfate; 1-5% phosphate; and 3-8% soybean meal. The concentrations of $MgSO_4$, $(NH_4)H_2PO_4$ and oil is important to optimum production of lipase activity. The initial pH must not be below 5.0.

Production in a fermenter requires some modifications. The medium components are as described for shake flasks, but it is necessary to use an intermediate step of inoculum to reduce the growing time to the interval of 3-5 days. The inoculum volume used is 5% (1 to 10) of a nutrient containing 4% whole wheat flour and 8% corn steep water at pH 5.5. The sterile inoculum nutrient is inoculated with the PDA slant and grown 30-50 hrs. at 30° C. and then transferred to the growing medium. Here, the oil may be corn or soy oil and the concentration may be from 1-6%. All of the oil can be present initially or added in increments after growth has started.

Preparing the Lipase

Filtering the fungal mycelium effectively isolates the lipase. The lipase activity of the crude culture when harvested (pH 4.5-5.0) is bound to the mycelium. The mycelium-free culture filtrate contains essentially no lipase activity (<5%), and all soluble extracellular components which may have a negative effect on cheese flavor.

Release of lipase activity from the mycelium into a second extraction filtrate depends on the concentration of the mycelium, the pH, the buffer salt concentration of the extraction filtrate (0.5-3.0% $PO_4$ at optimum pH), the concentration of surfactant (preferably <1%), and the treatment time.

FIG. 1 illustrates how the amount of lipase released to extraction filtrate using Ethofot 242/25 surfactants varies according to the concentration of mycelium. All of this data was obtained at pH 6.2. Optimal recovery of lipase from mycelium is achieved normally at pH 6.2 because the lipase (free from mycelium) shows excellent stability for long periods. As the pH increases the lipase is less stable, and it is actively destroyed above pH 7.5. For example, after 42 hours at 4°-5° C. filtrate showed 94%, 87% and 74% activity retention respectively at pH 6.3, 6.8 and 7.4. After treatment under optimal conditions, about 80-90% of the lipase activity can be recovered from the mycelium filtrate.

The lipase in the extraction filtrate can be used directly for cheese flavor modification or alternatively concentrated in vacuo or by ultrafiltration before cheese addition. The filtrate or concentrate can be dried in vacuum at 0°-35° C. or spray dried to produce a dry concentrate which can be blended with other components, e.g. sodium chloride, phosphates, etc., used routinely in cheese manufacture. The methods of concentration and drying are conventional techniques known to those of ordinary skill in the art.

Assaying Lipase Activity

Two different assays have been used for lipase activity. In the first, potentiometric titration is performed so as to determine lipase forestomach units (LFUs). One LFU equals the activity that releases 1.5µ mol of butyric acid per minutes, Food Chemical Codex 3rd Ed., National Acadamic Press, 1981.

The tiration substrate is prepared by dispering an amount of sodium caseinate equivalent to 600 mg of casein, in 95 ml of water contained in a one-half pint freezer jar that fits the head of a suitable high-speed blender. This is mixed with 0.5 gm of hydroxylated lecithin. Finally 5.0 ml of Tri-n-butyrin is added and mixed for 60 sec. at low speed. This substrate must be held to 33° C. and used within 4 hours.

The sample is prepared by suspending or dissolving an accurately weighed amount of enzyme in water.

To measure, the titrator is filled with 0.05N sodium hydroxide, and the instrument is calibrated following the manufacturer's instructions. The substrate is mixed for about 15 sec with a magnetic stirrer, then 20.0 ml is pippetted into the reaction vessel of the titrator. One ml of the sample is added and equilibrated for 15 min. The rate, in ml per min., at which the titrant was delivered during the titration, is determined and recorded as R. The activity of the enzyme is calculated by the formula:

$$LFU/g = R \times 0.025 \times 10^3/(W \times 1.25),$$

in which W is the weight, in g, of the enzyme preparation contained in the 1.0 ml of Sample taken for analysis.

It should be noted that the enzyme's ability to hydrolyze tricaproin (C6), tricaprylin (C8), tricaprin (C10), can be measured simply by replacing tri-n-butyrin with the desired substrate.

A second assay is the cream-acid titration method. An aliquot (20.0 ml) of 10.5% butterfat Half and Half is placed into 2 oz. glass jars and brought to 33° C. in thermostated water bath. After temperature equilibrium has been established (about 10 minutes), 1.0 ml of enzyme solution is added and incubated for 2 hours. Then 10 ml of ethanol (denatured formula 2A is suitable) is added to stop the reaction before titrating with 0.05N NaOH to pH 9.5. The titration should be carried out with a glass electrode and the incubation mixture plus alcohol should be stirred with a magnetic bar.

A substrate control (20 ml half and half plus 10 ml water) is run to correct for the amount of alkali required to neutralize the salts present in the cream.

An enzyme control is also run to correct for the amount of alkali required to neutralize the salts present in the enzyme.

The increase in acidity corresonding to a 1% hydrolysis of the butterfat is equivalent to a titration difference of 1.65 ml 0.05N NaOH. Activity is calculated from the following relationship:

$$CLU = \frac{0.05\ N\ \text{NaOH produced in 20 ml Substrate}}{\text{g Enzyme used}}$$

Effect of pH, Temperature and Time on Lipase Activity

Figure 3:
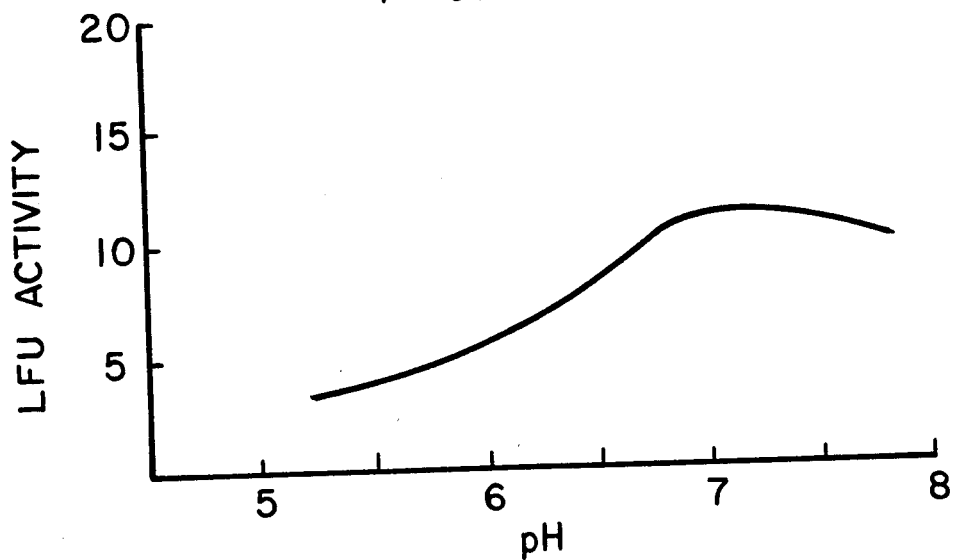
FIG. 3 is a graph showing the effect of pH on lipase activity at 33° C.

The effects of temperature and pH on tributryin hydrolysis by the present lipase is noted in FIGS. 2-4. As seen in FIG. 2, the optimum temperature for enzyme activity is approximately 42.5° C., while FIG. 3 shows that the optimum pH is close to 7.0. A sharp decrease in activity as the temperature is raised can be seen in FIG. 4, the effect being more dramatic with an increase in pH. The plots given in FIG. 5a-f also indicate that an increase in time accentuates the adverse effect of pH values above 6.2, although pH 7.0 is clearly optimal at temperatures below 60° C.

Triglyceride Hydrolysis

The present lipase has been used to hydrolyze specific triglycerides (tricaprylin, tricaproin, and tributyrin) into their respective free fatty acids (FFAs) (caprylic, caproic, and butyric acids. Conventional gas chromatography techniques can be used to measure these FFAs.

Hydrolysis has been measured in the following manner. Five gm of triglyceride is blended with 100 ml phosphate buffer (pH 6.5, 0.05 m) containing 1% gum arabic to form an emulsion, which is shaken with 2.0 ml of fungal lipase (100 mg) for 4 hours at 33° C. To stop the reactions, 10 ml of ethanol is added, and the resulting free fatty acids are measured by gas chromatography.

The free triglyceride hydrolysis results are as follows:

TABLE 2

| Enzyme Treated Substrate | % Free Fatty Acid | Ratio $(C\Delta)/C_4$ |
|---|---|---|
| Tributyrin (C4) | 3.39 | 1.00 |
| Tricaproin (C6) | 3.76 | 1.11 |
| Tricaprylin (C8) | 5.26 | 1.55 |

The present lipase hydrolyzes both tricaproin and tricaprylin more efficiently than it hydrolyses tributyrin. This type of hydrolysis can be demonstrated by taking a ratio of the two numbers $(C/C_4)$. Increased rate of hydrolysis can be shown by the ratio TC/TB. Typically, the increased rate of activity results in equivalent $C_8/C_4$ production. This specificity is unique for the present lipase.

The following table shows the tricaprylin (TC) to tributyrin (TB) hydrolysis ratio (TC/TB) for known lipases, as cited by known authors:

TABLE 3
RELATIVE ACTIVITY OF LIPASE PREPARATIONS AS CITED IN LITERATURE

| Preparation | Activity vs. Tributyrin | Activity vs. Tricaprylin | TC/TB | Cite |
|---|---|---|---|---|
| Hog pancreas | 100 | 37 | 0.37 | Enzymologia |
| Human milk | 100 | 59 | 0.57 | 11 178 (1944) |
| Bovine pancreas | 100 | 41 | 0.41 | |
| | mol % $C_4$ | mol % $C_8$ | | |
| *Release of FFA from Milk Fat* | | | | |
| Milk Lipase | 13.9 | 1.8 | 0.13 | Nelson J. H. |
| Steapsin | 10.7 | 1.5 | 0.14 | J$_{Amer}$ Oil |
| Pancreatic Lipase | 14.4 | 1.4 | 0.09 | Chem Soc |
| Calf Esterase | 35.0 | 1.3 | 0.04 | 49 559 |
| Esterase pancreatin | 15.83 | 3.0 | 0.19 | 1972 |
| Calf pregastric esterase | 40.8 | 8.6 | 0.21 | Farnham |
| Kid pregastric esterase | 50.0 | 8.4 | 0.17 | et al |
| Lamb pregastric esterase | 44.8 | 8.3 | 0.19 | 1956 |
| *% of Total Free Fatty Acids (microequivalent basis) after 3 hrs. at 35° C. on milk fat* | | | | |
| Imported crude kid rennet paste | 32.8 | 7.1 | 0.22 | Harper W. J. |
| Domestic purified calf rennet paste | 10.7 | trace | .00 | J. Dairy Sci |
| Calf oral lipase | 36.7 | 4.8 | 0.13 | 40 556 (1957) |
| Kid oral lipase | 44.4 | 7.6 | 0.17 | |
| Lamb oral lipase | 48.1 | 14.2 | 0.30 | |
| Aspergillus lipase | 43.1 | 20.2 | 0.47 | |
| Milk lipase | 13.5 | 10.2 | 0.76 | |
| Pancreatic lipase | 8.4 | trace | .00 | |
| *μ moles FFA liberated/ml enzyme* | | | | |
| *Syncephalastrum racemosum* | 11.2 | 7.6 | 0.68 | Chopra et al J. Dairy SC 65 1890 (1982) |
| *ml 0.1 N Acid Produced in 2 hrs. 30° C.* | | | | |
| *Penicillum roqueforti* | 1.45 | 0.56 | 0.39 | |
| *Aspergillus niger* | 1.20 | 2.18 | 1.82 | Shipe, W. F. Arch. Bioch. 30 |
| | | | 165 | (1951) |

FIGS. 6 and 7 illustrate the significantly better TC hydrolysis versus TB hydrolysis of the present lipase and how it can be increased with temperature. At 40° C. and pH 7.0 the TC/TB ratio is 1.73, while at 50° C. and pH 7.0 it is an even greater 2.49.

Milk Triglyceride Hydrolysis

The present lipase has been tested for hydrolysis of those triglycerides present naturally in milk. To test for hydrolysis, 180 ml of 10.5% butter fat cream is treated with 0.36 g (0.2%) and 0.90 g (0.5%) of either the present lipase or calf lipase. Samples are held for 15 days at 0°–3° C., before free fatty acid (C4 to C12) is determined by gas chromatography. A control cream sample without enzyme is carried also through the experiment.

The results of the milk test are as follows.

TABLE 4

| | Mg FFA/ml cream | | | | |
|---|---|---|---|---|---|
| Specific FFA | Control | 0.2% Present Lipase | 0.5% Present Lipase | 0.2% Calf Lipase | 0.5% Calf Lipase |
| C4  | 0.18  | 0.37  | 0.52 | 0.38 | 0.53 |
| C6  | 0.09  | 0.32  | 0.43 | 0.13 | 0.20 |
| C8  | 0.10  | 0.20  | 0.27 | 0.12 | 0.15 |
| C10 | 0.14  | 0.30  | 0.41 | 0.20 | 0.16 |
| C12 | <0.05 | <0.05 | 0.09 | 0.05 | 0.05 |

TABLE 5

| | % Hydrolysis of Specific Glyceride | | | | |
|---|---|---|---|---|---|
| Specific FFA | Control | 0.2% Present Lipase | 0.5% Present Lipase | 0.2% Calf Lipase | 0.5% Calf Lipase |
| C4  | 6.0  | 12.3 | 17.3 | 12.7 | 17.7 |
| C6  | 4.5  | 16.0 | 21.5 | 6.5  | 10.0 |
| C8  | 11.9 | 23.8 | 32.1 | 14.5 | 17.8 |
| C10 | 8.3  | 17.9 | 24.4 | 11.9 | 9.5  |
| C12 | <0.8 | <0.8 | 1.5  | 0.8  | 0.8  |

TABLE 6

| | % Hydrolysis of Specific Glyceride (Corrected for FFA present in Control) | | | |
|---|---|---|---|---|
| Specific FFA | 0.2% Present Lipase | 0.5% Present Lipase | 0.2% Calf Lipase | 0.5% Calf Lipase |
| C4  | 6.3  | 11.3  | 6.7 | 11.7 |
| C6  | 11.5 | 17.0  | 2.0 | 6.0  |
| C8  | 11.9 | 20.2  | 2.6 | 5.9  |
| C10 | 9.6  | 16.1  | 3.6 | 1.2  |
| C12 | 0    | (0.7) | 0   | 0    |

Although FFA production of the present lipase is nearly identical to that of calf lipase for C4 production, all of the other FFA data show that the present lipase hydrolyzes the glycerides of C6, and C8, and C10 to a much greater extent. For example the present lipase shows, respectively, 5.8×, 4.6×, 2.7× more C6, C8, C10 than the calf lipase at 0.20% concentration, and 2.8×, 3.4× and 13.4× at 0.50% concentration.

Triglyceride Hydrolysis in Oils

The present lipase has been tested also for production of 5% emulsions of soy, butter, and coconut oils. Chromatography of the treated emulsions (4 hours at 33° C.) reveals the ability of this lipase to hydrolyze a whole range of triglycerides. The level of certain triglycerides in the mixtures and the ability to fully emulsify the substrates can alter the rate of specific free fatty acid released as illustrated in Table 7.

| Fatty Acid Determined | Soy Oil % FFA | Butter Oil % FFA | Coconut Oil % FFA |
|---|---|---|---|
| C2    | **ND | ND    | ND    |
| C4    | ND   | 0.16  | ND    |
| C6    | ND   | 0.066 | 0.029 |
| C8    | ND   | 0.014 | 0.19  |
| C10   | ND   | 0.062 | 0.042 |
| C12   | ND   | 0.19  | 0.22  |
| C14   | ND   | 0.062 | 0.047 |
| C16   |      |       |       |
| C18   | 0.13 | 0.57  | 0.57  |
| C18-1 | 0.97 | 0.072 | 0.072 |
| C18-2 | 3.25 | 0.24  | 1.61  |

**ND = none detected

Cheese Preparation

Cheese has been made with the present lipase in the following manner. Milk is obtained from a diary farm, batch pasteurized at 145° F. for 30 minutes, and then held at 36° F. until the following day. (Colby cheese is made using Hansen CH 60Y ™ as a starter). Equivalent activity amounts of the present lipase and Miles 600 calf lipase (by cream assay) are preweighed and mixed with salt to give 2% salt by weight. Eight treatments of the cheese are made using 20 pound blocks. Control blocks with salt but without enzyme are made as well.

The resulting cheeses are sampled at 1, 28, 72, 102, and 198 days. They are evaluated organoleptically and analyzed for free fatty acids by gas chromatography, known acid degree value (ADV) tests, and also by 12% TCA soluble nitrogen tests.

After 72 hours, the cheeses having 0.048% present lipase and 0.128 calf lipase have about the same ADV and total FFA, which is 50–70% greater than that of the control. However, at 102 and 198 days, the concentrations of enzyme used (and for which data has been tabulated) are too high for good flavor in that too much free fatty acid has developed. The calf lipase produces too much butyric acid, and the present lipase, too much total free fatty acid C14–C18.

At lower concentrations (0.012 and 0.024%) the present lipase gives good aged flavor without rancidity associated with butyric acid at 102 days. The control has weak flavor at this point, while the calf lipase showed the typical rancidity associated with butyric acid at days, even with low levels of the enzyme preparation (0.064 and 0.032%).

Figure 8:
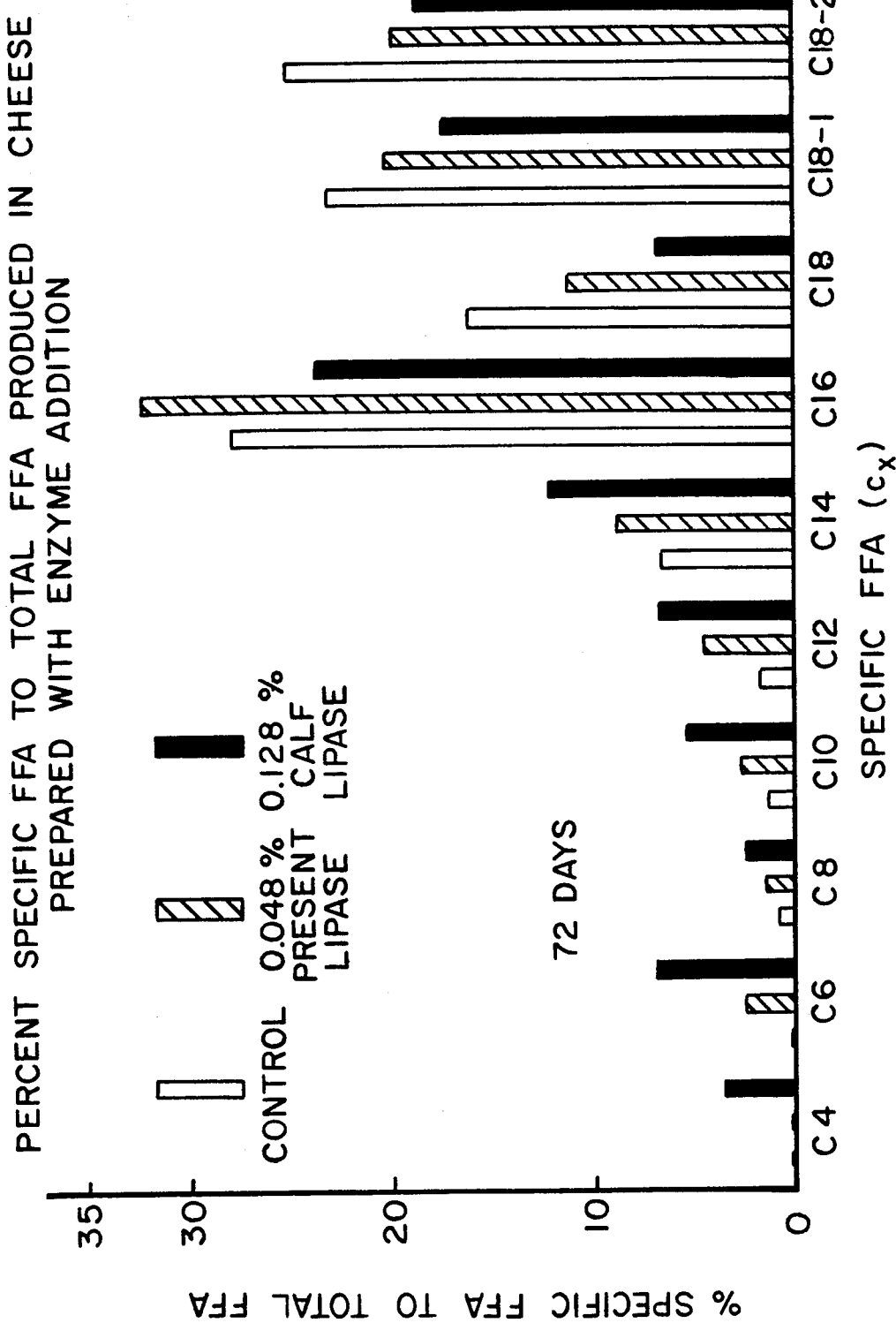
FIG. 8 is a graph showing the percent hydrolysis of a specific free fatty acid to total free fatty acid in enzyme-added cheeses.

FIGS. 8 and 9 illustrates the triglyceride hydrolysis data for the control cheese and cheeses prepared with 0.048% NM 313 lipase and 0.128% calf lipase. It is readily apparent that at 72 days and 102 days, the butyric acid content in cheese made from the calf lipase is very elevated over that of the control. On the other hand, cheese made with the present lipase is more like the control cheese as far as butyric acid levels.

The present lipase reduces the mild cheese aging process by 2–5 times. At 102 days the present lipase-added cheese shows greater C16, C18, C18-1 and C18-2 content than the control cheese, indicating an acceleration (i.e. more rapid flavor development) of the usual ripening process. Thus, cheeses manufactured with the present lipase develop a Cheddar like flavor while those of the calf lipase produces an Italian type flavor. It is apparent that the lipase derived from the present Aspergillus organism is unique in shortening the storage time needed for Cheddar and other mild flavored cheeses.

Having described the invention with particular reference to preferred form, it will be obvious to those skilled in the art to which the invention pertain, that, after understanding the invention, various changes and modifications may be made without departing from the spirit and scope of the invention as defined by the appended claims.

I claim:

1. A biologically pure culture of a variant of Aspergillus species which produces a lipolytic enzyme having a tricaprylin to tributyrin hydrolysis ratio greater than 1.5.

2. A lipolytic enzyme derived from an organism belonging to the Aspergillus species which has a tricaprylin to tributyrin hydrolysis ratio of at least 1.5.

3. An improved methods of producing mild cheeses with characteristically low butyric acid content, the improvement comprising adding to the cheese curd or milk an effective amount of lipolytic enzyme having a tricaprylin to tributyrin hydrolysis ratio of at least 1.5, whereby the aging of the cheese is accelerated.

4. The method of claim 3 wherein the mild cheese is cheddar cheese.

5. The method of claim 3 wherein protease is added in an amount effective to soften the cheese.

6. An improved method of producing cheese, the improvement comprising adding to the cheese curd or milk an effective amount of a first lipolytic enzyme having a tricaprylin to tributyrin hydrolysis ratio of at least 1.5 and a second lipolytic enzyme with a tricaprylin to tributyrin hydrolysis ratio of less than 1.5.

7. The method of claim 6 wherein a protease is added in an amount effective to soften the cheese.

8. The method of claim 3 wherein the lipolytic enzyme is derived from a strain of Aspergillus species.

* * * * *